(12) United States Patent
Yeats et al.

(10) Patent No.: US 10,166,311 B1
(45) Date of Patent: Jan. 1, 2019

(54) TWIST ACTIVATED DISPENSER

(71) Applicants: Shawn P. Yeats, Lehi, UT (US); Haruyoshi Miyagi, Lehi, UT (US)

(72) Inventors: Shawn P. Yeats, Lehi, UT (US); Haruyoshi Miyagi, Lehi, UT (US)

(73) Assignee: F-MATIC, INC., Lehi, UT (US)

( * ) Notice: Subject to any disclaimer, the term of this patent is extended or adjusted under 35 U.S.C. 154(b) by 0 days.

(21) Appl. No.: 15/788,705

(22) Filed: Oct. 19, 2017

(51) Int. Cl.
*A61L 9/12* (2006.01)

(52) U.S. Cl.
CPC ............... *A61L 9/127* (2013.01); *A61L 9/12* (2013.01)

(58) Field of Classification Search
CPC ................................ A61L 9/127; A61L 9/12
USPC ............... 239/44, 45, 46, 47, 51, 51.5, 57
See application file for complete search history.

(56) References Cited

U.S. PATENT DOCUMENTS

| | | | | |
|---|---|---|---|---|
| 4,161,284 A | * | 7/1979 | Rattan | A61L 9/12 239/43 |
| 4,165,835 A | * | 8/1979 | Dearling | A61L 9/12 239/45 |
| 4,526,320 A | * | 7/1985 | von Philipp | A01M 1/2044 239/34 |
| 4,917,301 A | * | 4/1990 | Munteanu | A61L 9/01 239/43 |
| 5,000,383 A | * | 3/1991 | van der Heijden | A01M 1/2044 239/44 |
| 5,749,520 A | * | 5/1998 | Martin | A01M 1/2044 239/34 |
| 5,875,968 A | * | 3/1999 | Miller | A61L 9/127 239/44 |
| 6,553,712 B1 | * | 4/2003 | Majerowski | A01M 1/2011 239/44 |
| 6,957,779 B2 | | 10/2005 | Joshi et al. | |
| 7,614,568 B2 | | 11/2009 | Joshi et al. | |
| 7,857,236 B2 | | 12/2010 | Zlotnik et al. | |
| 8,005,350 B2 | | 8/2011 | Zlotnik et al. | |
| 9,015,989 B1 | * | 4/2015 | Zeamer | A01M 1/2005 239/37 |
| 9,238,086 B2 | | 1/2016 | Sidawi | |
| 9,468,697 B2 | * | 10/2016 | Gruenbacher | A61L 9/04 |
| 2018/0043048 A1 | * | 2/2018 | Sidawi | A61L 9/127 |

* cited by examiner

*Primary Examiner* — Christopher Kim
(74) *Attorney, Agent, or Firm* — Jeffery M. Lillywhite, PC

(57) ABSTRACT

A dispenser includes a container for storing a fluid. The container has a seal at a discharge end that is made from a material capable of being penetrated. A lid is fixedly attached to a closed end of the container. The lid has a set of vents arranged on the lid beyond an outer wall of the container. An absorbing device is disposed around the outer wall of the container. A cage structure includes the lid and a base. The cage structure is attached to the lid and base and is combined to enclose the container and absorbing device. The base includes a set of blades that are positioned inside the base and aligned with the seal in the container. The cage structure includes a set of ramps and the base includes a set of tabs. The base is placed in the cage structure with the tabs configured to slide along each ramp when the base is rotated with respect to the cage structure to draw the base and cage structure together. As the base is rotated, the set of blades travel into the container and puncture the seal.

20 Claims, 9 Drawing Sheets

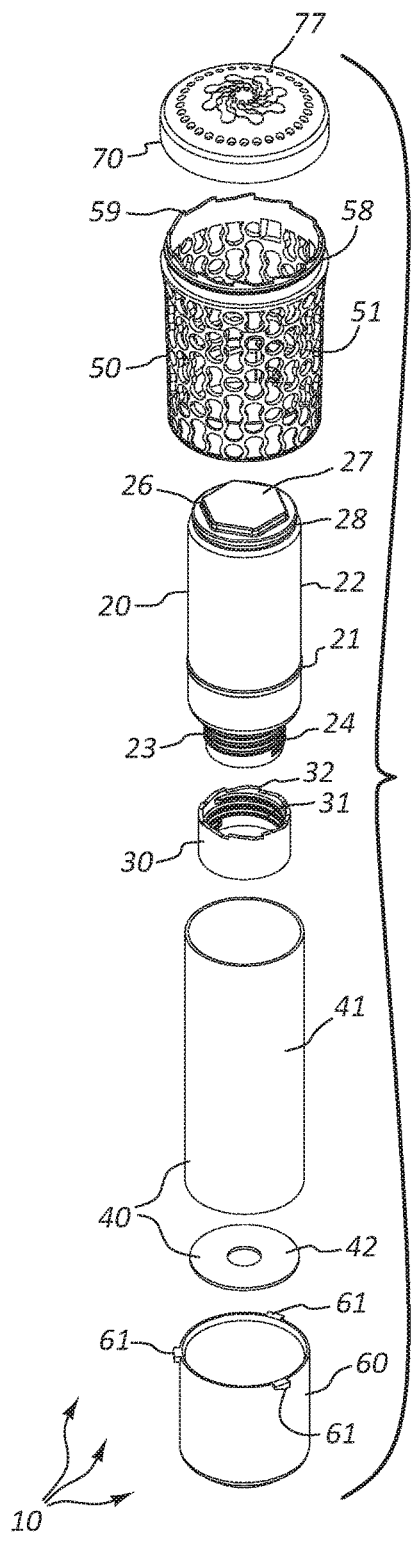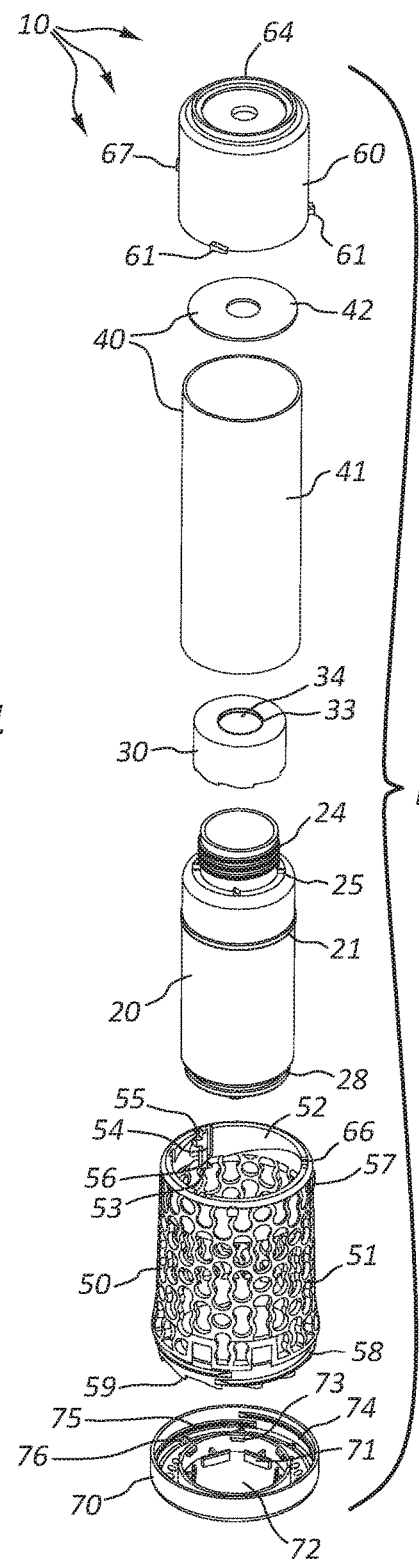

TWIST ACTIVATED DISPENSER

CROSS-REFERENCE TO RELATED APPLICATIONS

Not applicable.

BACKGROUND OF THE INVENTION

1. The Field of the Invention

This invention relates to twist activated dispensers containing an aromatic liquid and a wetted wick, and more specifically, to an air freshener canister with twist activation to release the aromatic liquid within the canister to be absorbed by the wick.

2. The Relevant Technology

Various dispensers have been used to disperse liquids fragrances into the air over an extended period to the surrounding environment. One such device, disclosed in U.S. Pat. No. 6,957,779 to Ashok V. Joshi, et al., is a framed fluid-delivery device that includes a cartridge within a frame assembly. The frame retains the cartridge for time-release delivery of a fluid from a dispersion pad that is placed in the frame. The fluid is delivered onto the dispersion pad, which volatilizes over time. A piercing member punctures a breakable seal on the cartridge, initiating the fluid delivery onto the dispersion pad. Piercing member is a single, self-contained piece having base with a piercing point. The piercing point passes upward and through the breakable seal. The piecing point includes sloped surfaces to flow the fluid out of the cartridge and away from the piercing point to and into the dispersion pad.

A base portion has an outer frame and cross beams to provide structural support. Base portion additionally includes a structure for facilitating the delivery of fluid released from fluid-delivery cartridge out and away from frame assembly, such as pre-scored, puncture-ready shapes. Once pierced and split by piercing member, the fluid is released from the cartridge into the dispersion pad.

The fluid-delivery cartridge includes a fluid delivery device such as a gas generating cell, which produces a gas as a product of an electrochemical reaction. A shield may be necessary for the prolonged life of gas generating cell. The shield is placed between gas generating cell and a fluid reservoir to prevent the influx of fluid into gas generating cell. The gas generating cell is used to help push the gas generated within cell out into the housing.

In another example, as illustrated by U.S. Pat. No. 8,005,350 to Arnold H. Zlotnik, et al., an aromatic odor neutralizer includes a vaporization chamber containing a wick. The vaporizer includes evaporation chamber having an elongated tubular configuration to partly wrap the wick, yet exposing the volatile liquid with the wick to ambient air flow. The wick is formed in a cylindrical cavity between a vessel containing the supply of volatile liquid and a cylindrical ventilating housing. A liquid storage cup provides a reservoir for the volatile liquid that is dispensed from the vessel. A portion of the wick is immersed in the volatile liquid of the liquid storage cup.

A tubular knife edge projects in an upstanding manner from a bottom wall of the cup to pierce a weaken end wall section. Once pierced, the volatile liquid flows into the storage cup until it equalizes between the fluid in the vessel and the reservoir. The liquid in the reservoir may spill if not handled properly.

In a more recent example, as shown in U.S. Pat. No. 9,238,086 to Rami Sidawi, an air freshener canister is spill-resistant. The canister includes two main components: a supply vessel filled with aromatic liquid; and an evaporator cage with a cylindrical wick. To activate the air freshener canister, the supply vessel is inserted into the cage where a cylindrical inner sleeve having a socket is engaged with a threaded mouth of the supply vessel. As the supply vessel is tightened into the socket, a projecting blade slices through a membrane to release an aromatic liquid from the supply vessel and wet the cylindrical wick. The liquid flows out in a radially direction to the exterior of the cylindrical sleeve and into the cylindrical wick. The air freshener canister is spill resistant, but requires some assembly.

The subject matter claimed herein is not limited to embodiments that solve any disadvantages or that operate only in environments such as those described above. Rather, this background of the relevant technology is only provided to illustrate one exemplary technology area where some embodiments described herein may be practiced.

BRIEF SUMMARY

According to one example, a dispenser includes a container for storing a fluid. The container has a seal at a discharge end that is made from a material capable of being penetrated. A lid is fixedly attached to a closed end of the container. The lid has a set of vents arranged on the lid beyond an outer wall of the container. An absorbing device is disposed around the outer wall of the container. A cage structure includes the lid and a base. The cage structure is attached to the lid and base and is combined to enclose the container and absorbing device. The base includes a set of blades that are positioned inside the base and aligned with the seal in the container. The cage structure includes a set of ramps and the base includes a set of tabs. The base is placed in the cage structure with the tabs configured to slide along each ramp when the base is rotated with respect to the cage structure to draw the base and cage structure together. As the base is rotated, the set of blades travel into the container and puncture the seal.

In another example, a dispenser includes a container for storing a fluid. The container includes a cap with a breakable seal. The cap is attached to the container at a first end. The lid is fixedly attached to a second end of the container. The lid has a set of vents. An absorbing device is disposed around the outside of the container and cap. A cage structure is attached to the lid and a base. The cage structure, lid and base collectively are configured to enclose the container, cap and absorbing device. The base includes a set of blades positioned inside the base and aligned with the breakable seal in the cap. The cage structure and base are connected with a rotational connection. When rotated with respect to each other, the cage structure and base are drawn together, collapsing the dispenser on itself and pulling the set of blades into the container and puncturing the breakable seal.

In further example, a dispenser includes a container for storing a fluid. The container includes a seal at a discharge end. The seal is made from a material capable of being penetrated. An absorbing device includes a wick disposed around an outer wall of the container. A cage structure includes a mesh portion, a lid and a base, the lid being fixedly attached to a closed end of the container and a first end of the mesh portion, the base being rotationally attached to a second end of the mesh portion. The cage structure is configured to enclose the container and absorbing device. The mesh portion is configured to allow air to flow into the cage structure around the wick. The base includes a set of blades positioned inside the base and aligned with the seal in the container. The container includes a rib formed around the container that is configured to create a snug fit between the container and the wick.

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

Additional features and advantages will be set forth in the following description and in part will be obvious from the description or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 1 is an exploded isometric view of a twist activated dispenser in an upright position;

FIG. 2 is an exploded isometric view of the twist activated dispenser in an inverted position;

DETAILED DESCRIPTION OF THE PREFERRED EMBODIMENTS

Figure 3:
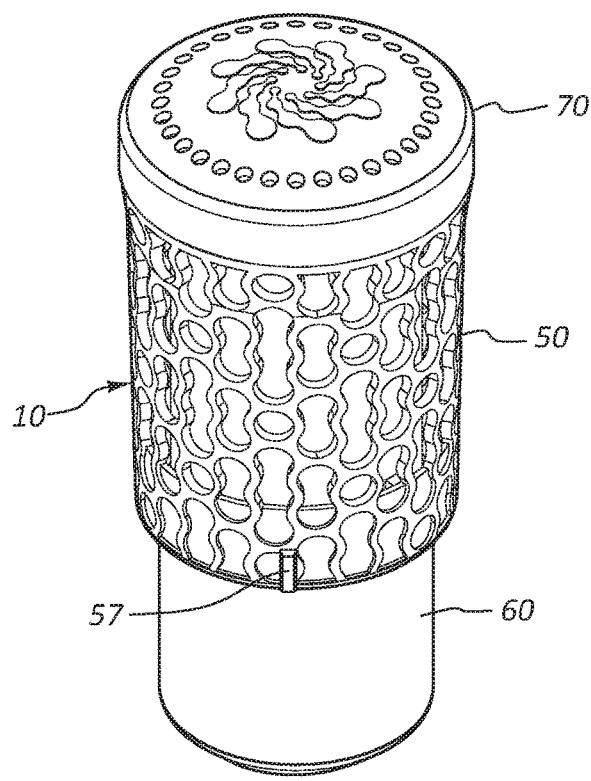
FIG. 3 is a top isometric view of the twist activated dispenser.

The invention will now be described in detail with reference to the attached drawing figures. It is to be understood that the drawings are not necessarily drawn to scale and that they are intended to be merely illustrative.

Referring to FIGS. 1-10, a twist activated dispenser 10 is illustrated in accordance with the various embodiments of the invention. The twist activated dispenser 10 includes a container 20, an absorbing device 40 and a cage structure 50. The container 20 is configured to store a fluid, such as an aromatic liquid or fragrance. When the dispenser 10 is activated, the fluid releases from the container 20 and the absorbing device 40 takes up the fluid. As air passes through the cage structure 50, the fluid evaporates from the absorbing device 40 into the air.

The container 20 includes a rib 21 on an outer wall 22 of the container 20. The rib 21 restricts the fluid from passing a certain point along the outer wall 22. One end of the container 20 includes a fastening apparatus 23, such as threads 24 having barb mechanism 25 to prevent backing off, and the other end includes a locking device 26, such as a socket head 27 and locking rings 28.

A cap 30 is placed on one end of the container 20 to seal the fluid within the container 20. The cap 30 is attached to the container 20 with a matching fastening apparatus 23. In this embodiment, the threads 24 engage matching threads 31 in the cap 30. For example, the container 20 may include three threads and the cap may include three threads that are sized to match and thread into each other. The container 20 and cap 30 may also include a locking mechanism 32. In one example, the edge of the cap 30 includes a series of teeth 32 that engage with the barb mechanism 25 as the cap 30 is installed on the container 20 using the threads 24 to twist on and engage with the matching threads 31. Once tightened, the barb mechanism 25, such as four barbs spaced evenly around the neck of the container 20, engage with the teeth 32 to prevent the cap 30 from loosening or backing off. For example, the cap 30 may include eight teeth 32 equally spaced along an edge of the cap 30. The locking mechanism 32 prevents the fluid from accidentally spilling out of the container 20 while the dispenser 10 is being transported or stored.

The cap 30 includes an aperture 33 for displacing the fluid. The aperture 33 is covered with a seal 34, such as a foil or other material capable of sealing the fluid until cut, punctured or otherwise penetrated. The seal 34 prevents the fluid from escaping through the aperture 33 while unbroken. The seal 34 is attached to a discharge end of the container or the end of the cap 30 with an adhesive.

An absorbing device 40 includes a wick 41 and a pad 42. The wick 41 can be a fibrous sheet rolled into a cylinder, or any other material that sufficiently absorbs the fluid stored in the container 20. The absorbing material 40 can also be formed or molded into a cylindrical shape, or a shape formed to match the outer wall of the container 20. The inner wall of the wick 41 is configured to fit against the rib 21 encircling the container 20. The wick 41 and rib 21 are configured to create a snug fit around the container 20. The wick 41, when pressed against the rib 21, prevents the fluid from flowing out of the container 20 and up beyond the rib 21. The fluid, instead, is absorbed into the absorbing device 40, which may absorb beyond the position of the rib 21.

The pad 42 is disposed next to the cap 30 to absorb the initial flow of the fluid and prevent short-circuiting. The fluid flows into the pad 42 then towards the wick 41. The pad 42 can be made of a fibrous sheet, or any other material that sufficiently absorbs the fluid stored in the container 20. The pad 42 is placed against the cap 30. The pad 42 may have a washer or ring shape to provide a hole or space for the seal 34 to be punctured through the pad 42.

A cage structure 50 encloses the container 20 and absorbing device 40. The cage structure 50 includes a lid 60 and a base 70. The cage structure 50 has a mesh 51 or mesh portion to allow air to flow through the cage structure 50 and interact with the absorbing device 40 to evaporate the fluid. The mesh 51 or mesh portion may, for instance, have a circular, square, diamond, peanut or other fanciful design to allow air to flow into the cage structure 50. Other apertures or holes may be configured within the mesh 51 to allow the cage structure to be attached to a wall attachment or other mounting device or stand. For example, the cage structure may include two square holes formed in a top edge of the mesh to provide a connection point for hooks on a mounting device or stand to be connected to the dispenser.

A set of ramps 52 are positioned inside the cage structure 50. In one example, three ramps are molded into the inside of the cage structure 50 and spaced apart from each other. A stop 53 is placed at the end of or in-between each ramp 52. The stop 53 may include a blocking wall 54, a storage lock 55 and a locking groove 56, which are discussed in further detail below. An alignment marker 57 may be placed on the outside of the cage structure 50 to assist the user in determining the setting of the dispenser 10.

The mesh 51 includes a fastening mechanism having threads 58 and locking teeth 59 positioned on an end opposite the ramps 52. The threads 58 are formed in the outside of the cage structure 50 to attach the lid 70 to the cage. The lid is fixedly attached to a closed end of the container. The locking teeth 59 are provided to prevent the lid 70 from loosening or backing off. For example, the cage structure 50 may include 12 locking teeth 59 and two rows of threads 58 arranged along a top edge of the cage structure 50.

The cage structure includes a base 60 slidably connected to the set of ramps 52. The base 60 has a set of tabs 61 that are attached to the outer wall of the base and are configured to engage and slide along the corresponding ramp 52. Each tab 61 is separate from the other. When the base 60 is rotated with respect to the mesh 51, each tab 61 slides along the corresponding ramp 52 until the tab 61 engages with the stop 53. The stop 53 may be configured to prevent accidental movement from the ramp 52. The stop 53 includes a blocking wall 54 that is configured to prevent further rotation of the tab 61 beyond the ramp 52. The storage lock 55 is configured to prevent the tab 61 from moving vertically when being stored, or to prevent the base 60 from being pressed up into the mesh 51. The locking groove 56 is configured to lock the tab 61 in place once the dispenser 10 is activated. The locking groove 56 is sized to fit the length of the tab 61.

In operation, the tab 61 slides, from the storage lock 55, up the ramp 52 until the tab 61 hits the stop 53 where the tab slips into the locking groove 56. The locking groove 56 can be configured to be a recess below the top of the ramp 52. Each tab 61 can be configured to have a tapered shape to match the angle of the ramp 52 and to provide a smooth movement along the ramp 52. Each tab 61 may also have a constant thickness and be set at an angle to match the angle of the ramp 52.

Figure 7:
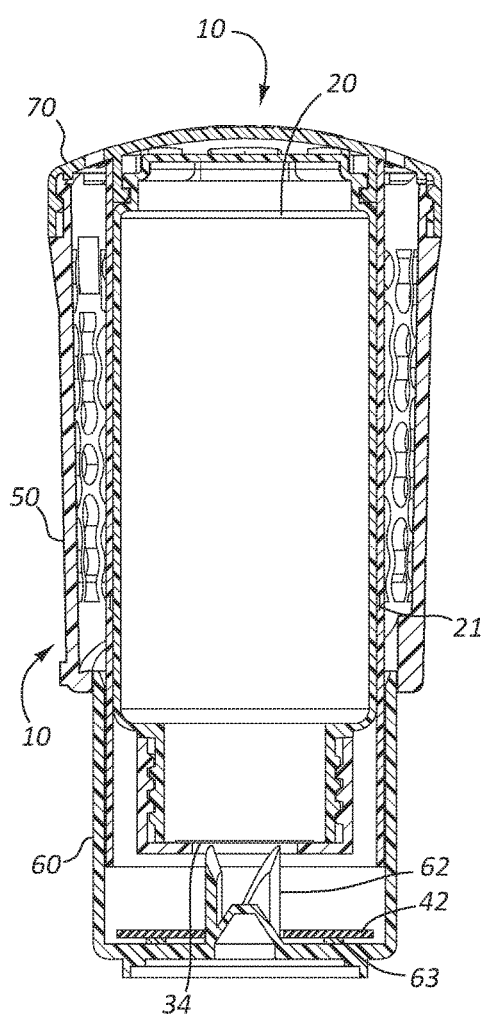
FIG. 7 is a cross-sectional view of the twist activated dispenser.
Figure 8:
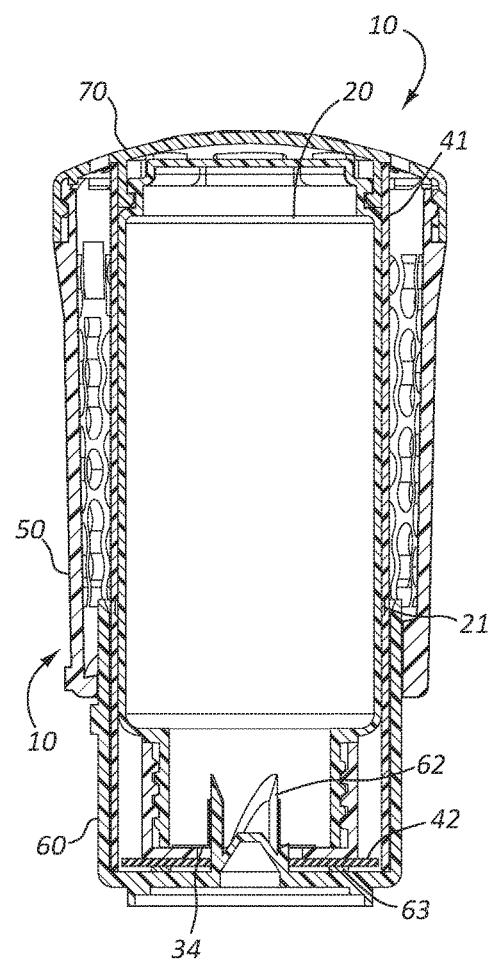
FIG. 8 is a cross-sectional view of the twist activated dispenser in the activated position.
Figure 10:
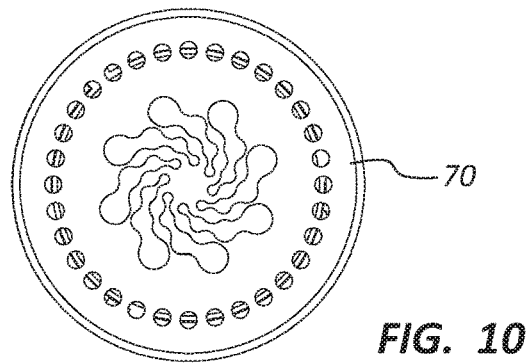
FIG. 10 is a top view of the twist activated dispenser.
Figure 9:
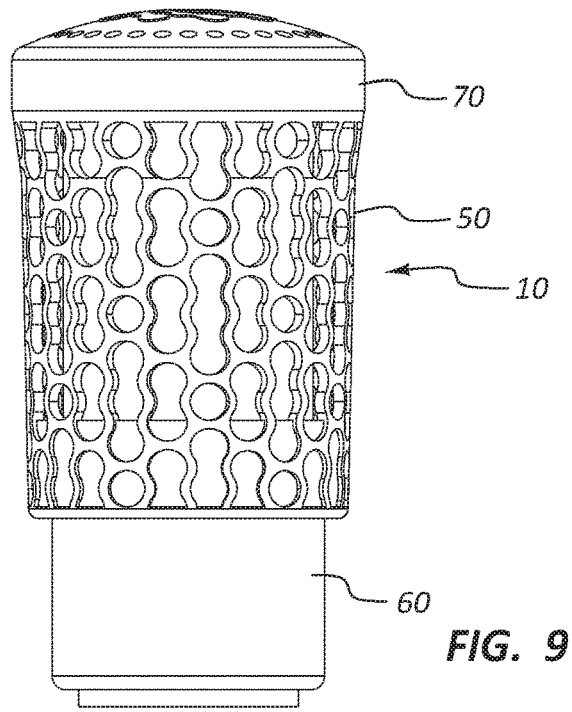
FIG. 9 is a side view of the twist activated dispenser.
Figure 11:
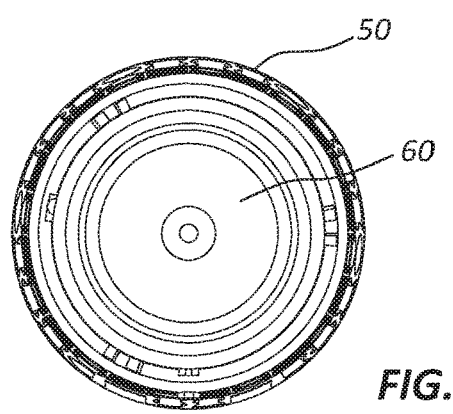
FIG. 11 is a bottom view of the twist activated dispenser.

The base 60 includes a set of blades 62 and can include a set of spacers, as shown in FIGS. 7 and 8. The blades 62 are positioned to cut or puncture the seal 34 in the cap 30 to allow the fluid to exit the container 20. The spacers 63 may be dispersed around the base 60 to provide a gap between the floor of the base and the pad 42 and allow more fluid to flow to the wick 41. In one example, the set of spacers 63 include three spacers equally spaced around the blades 62 on a radial line. The blades 62, for example, may include three blades, together forming a circular shape, and the aperture 33 on the cap 30 may be sized to have a diameter that is slightly larger than the blades 62. The pad 42, for instance, may have a hole formed in the center and sized to fit around the blades 62, the same size as the aperture 33 or slightly larger than the aperture 33.

The base 60 may also include a ridge 64 and alignment cone 65 to provide guides for attaching the dispenser 10 to a mount or stand. The alignment cone 65 is centered between the set of blades 62 to define a center of the base 60. The ridge 64 is placed on the outside of the base 60 and is configured to match a groove in a mount or stand, not shown.

The lid 70 is fixedly attached to the container 20 using the locking device 26. The lid 70 includes a set of walls 71 that form a socket 72. The socket 72 is configured to match with the socket head 27 of the container 20. The lid 70 includes a set of pressure fitting tabs 73 that are designed to interlock with the locking rings 28 formed in the container 20. To attach the lid 70 to the container 20, the lid 70 is aligned with the socket 72 and socket head 27 and pressure fit onto the container 20. For example, the socket head 27 may have a hexagonal shape and the socket 72 may include six walls to match the edges of the hexagon. The locking tabs 73 snap fit in-between the locking rings 28 to fixedly attach the lid 70 to the container 20. For example, the container may include two locking rings with a space between the rings to allow the locking tabs to fit between the rings and lock the lid in place.

The lid 70 includes a locking fastener 74 to attach the lid 70 to the cage structure 50. The locking structure 74, for example, can include threads 75 and barbs 76. The threads 75 are configured to match with the threads 58 of the cage structure 50. The barbs 76 are positioned to engage with the locking teeth 59 of the cage structure 50 when the lid 70 is threaded onto the cage structure 50. The lid 70, already attached to the container 20, is fastened to the cage structure by threading the lid 70 onto the cage structure 50 until the locking fastener 74 is engaged and locked into place. The lid 70 includes a series of vents 77, such as apertures or holes to enhance the air flow through the cage structure 50 and increase the effectiveness of the dispenser 10 to release fragrances into the air. For example, the lid 70 may contain about 32 holes equally spaced around the lid 70 in a circle outside the upper edge of the wick 41. The set of vents 77 are arranged on the lid 70 beyond the outer wall of the container 20 to be positioned between the cage structure 50 and the container 20.

While the dispenser 10 may be assembled in differing order, one example is discussed below. To assemble the dispenser 20, the base 60 is attached to the cage structure 50 by inserting the base through the end opposite the ramps 52, through the cage structure 50 and out the other end until the tabs 61 engage the storage lock 55. The base 60 may require a groove 66 if the base 60 includes an alignment marker 67 that protrudes out from the outer wall of the base 60. The alignment marker 67 is aligned with the groove 66 to slide the base 60 through the cage structure 50. Alternatively, the alignment markers 57 and 67 may be configured to be flush using a printed, engraved or decal marker, or other method of placing an image on a surface known in the art. If the alignment marker 67 is flush with the outer wall of the base 60, the groove 66 is not required.

The pad 42 is placed through the cage structure 50 and set in the base 60 around the set of blades 62. The container 20 is filled with a fluid and the cap 30 with the seal 34 is fastened to the container 20 to store the fluid in the container 20. The fluid is fully contained and spill-resistant within the container 20. The lid 70 is press fit onto the end of the container 20 opposite the cap 30. The wick 41 is placed around the container 20 by sliding the wick 41 over the container 20 from the end with the cap 30. The container 20 with the wick 41 is then inserted into the cage structure 50 and the lid 70 is screwed or threaded onto the cage structure 50 until the locking fastener 74 is engaged. The dispenser is a single, self-contained unit, which requires no assembly by the consumer to use.

Figure 4:
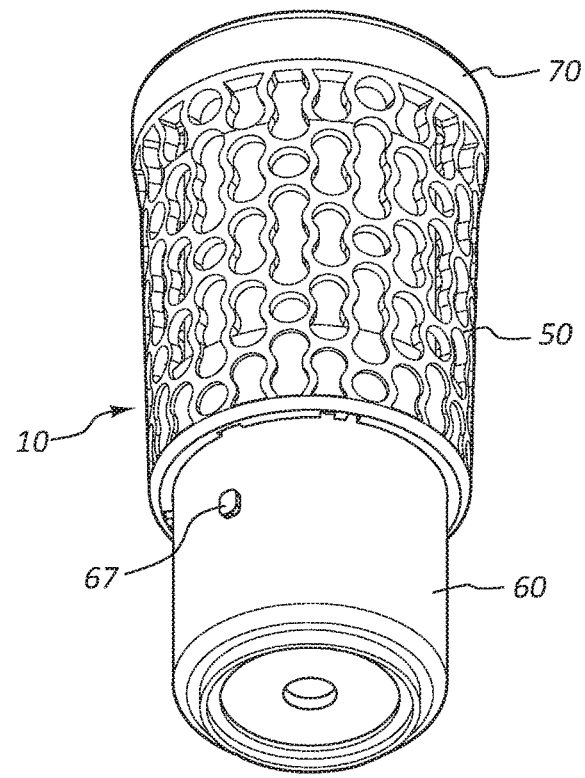
FIG. 4 is a bottom isometric view of the twist activated dispenser.

FIGS. 3 and 4 illustrate the dispenser 10 in a stored or inactive position. The alignment markers 57 and 67 in this position are not aligned. In the inactive position, the set of blades 62 are positioned below the seal 34, with the seal 34 unbroken, as shown in FIG. 7. The tabs 61 are placed in the storage lock 55 of the cage structure 60.

Figure 5:
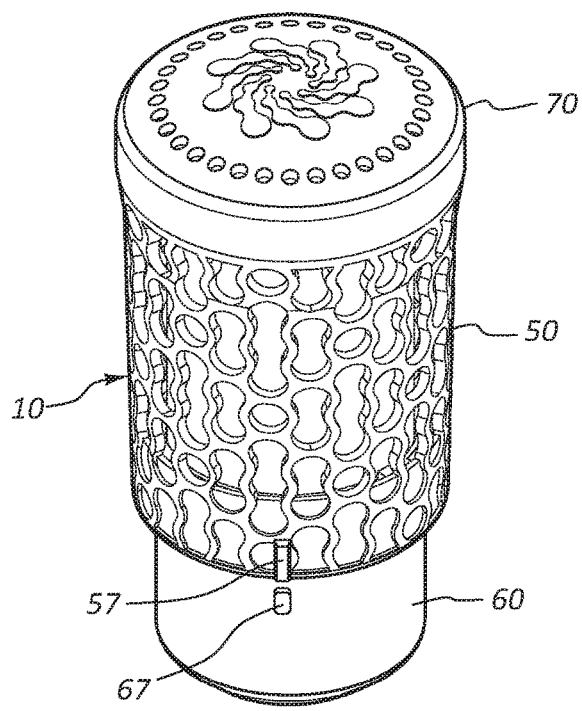
FIG. 5 is a top isometric view of the twist activated dispenser in an activated position.
Figure 6:
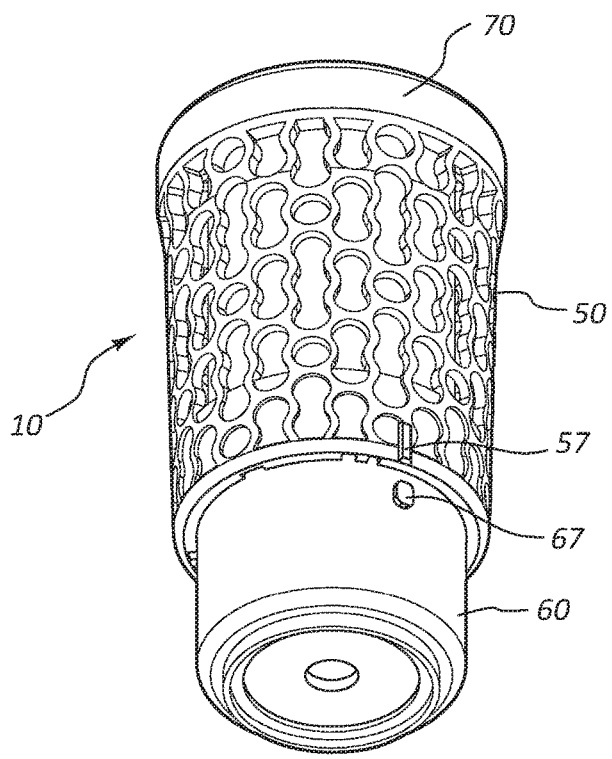
FIG. 6 is a bottom isometric view of the twist activated dispenser in the activated position.

To active the dispenser 10, as shown in FIGS. 5 and 6, the base 60 is twisted with respect to the cage structure 50 until the alignment markers 57 and 67 are aligned. A slight snap or engagement can be felt as the markers 57 and 67 are aligned. The tabs 61 of the base 60 travel along the ramps 52 pulling the base 60 and the blades 62 up to puncture or break the seal 34. For example, the base 60 may include three tabs 61 equally spaced around the top edge of the base 60 and the cage structure 50 may include three ramps 52 formed in the inside wall of the cage structure that are equally spaced to match the location of the tabs 61. The cage structure 50, for instance, may have three stops 53 formed in the inside wall of the cage structure 50 and positioned between each ramp 52 so that one side of the stop is paced at the beginning of one ramp and the end of another ramp.

The tabs 61 hit the stop 53, and more specifically, the blocking wall 54 and fall into the locking groove 56 to provide an engaging snap. The tab 61 rests in the locking groove 56 to prevent further movement of the base 60 with respect to the cage structure 50. FIG. 8 illustrates the dispenser 10 in the active position with the seal 34 punctured or broken. The set of blades 62 are pressed up through the aperture 33 breaking the seal 34 and allowing the fluid to flow out of the container 20 and absorbed by the wick 41 and pad 42. A space is provided between the container 20 and wick 41 to allow the fluid to accumulate in a pool or reservoir. The rib 21 formed around the container 20 maintains the height of the reservoir, preventing the fluid from pooling up beyond the rib 21. The rib 21 is positioned on the container and aligned with the bottom edge of the mesh 51 or mesh portion in the cage structure. The placement of the rib 21 below the mesh 51 or mesh portion enhances the amount of fluid that is absorbed by the wick 41 before a point where the fluid is evaporated into the air. The placement of the rib 21 improves the efficiency of the dispenser 10.

Figure 13:
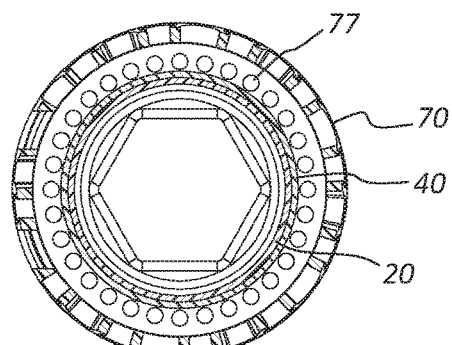
FIG. 13 is a sectional view taken along the lines 13-13 of FIG. 12.
Figure 12:
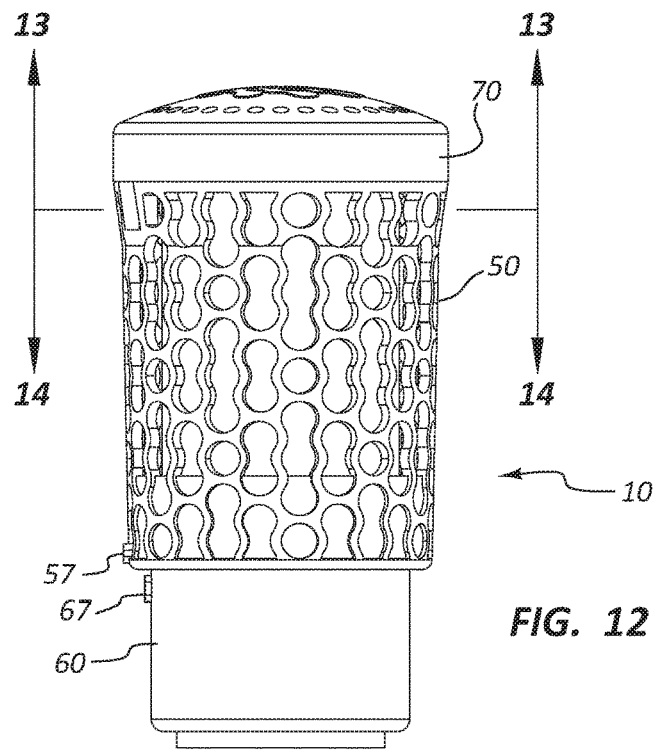
FIG. 12 is another side view of the twist activated dispenser.
Figure 14:
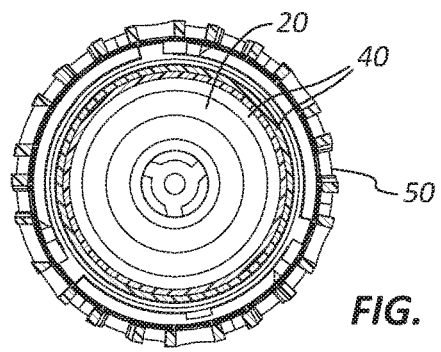
FIG. 14 is a sectional view taken along the lines 14-14 of FIG. 12.

The absorbing device 40 is illustrated in more detail in FIGS. 12-14. The vents 77 are arranged in a series around the lid 70. The vents 77 are placed on a radial line next to, but just beyond the absorbing device 40 to direct the air flow through the cage structure 50 and out the vents 77 to enhance the fluid evaporation from the absorbing device 40 into the air. The fluid flows from the container 20 onto the absorbing device 40. A distance is provided between the absorbing device 40 and the cage structure 50 to allow air to flow through the dispenser 10.

Figure 15:
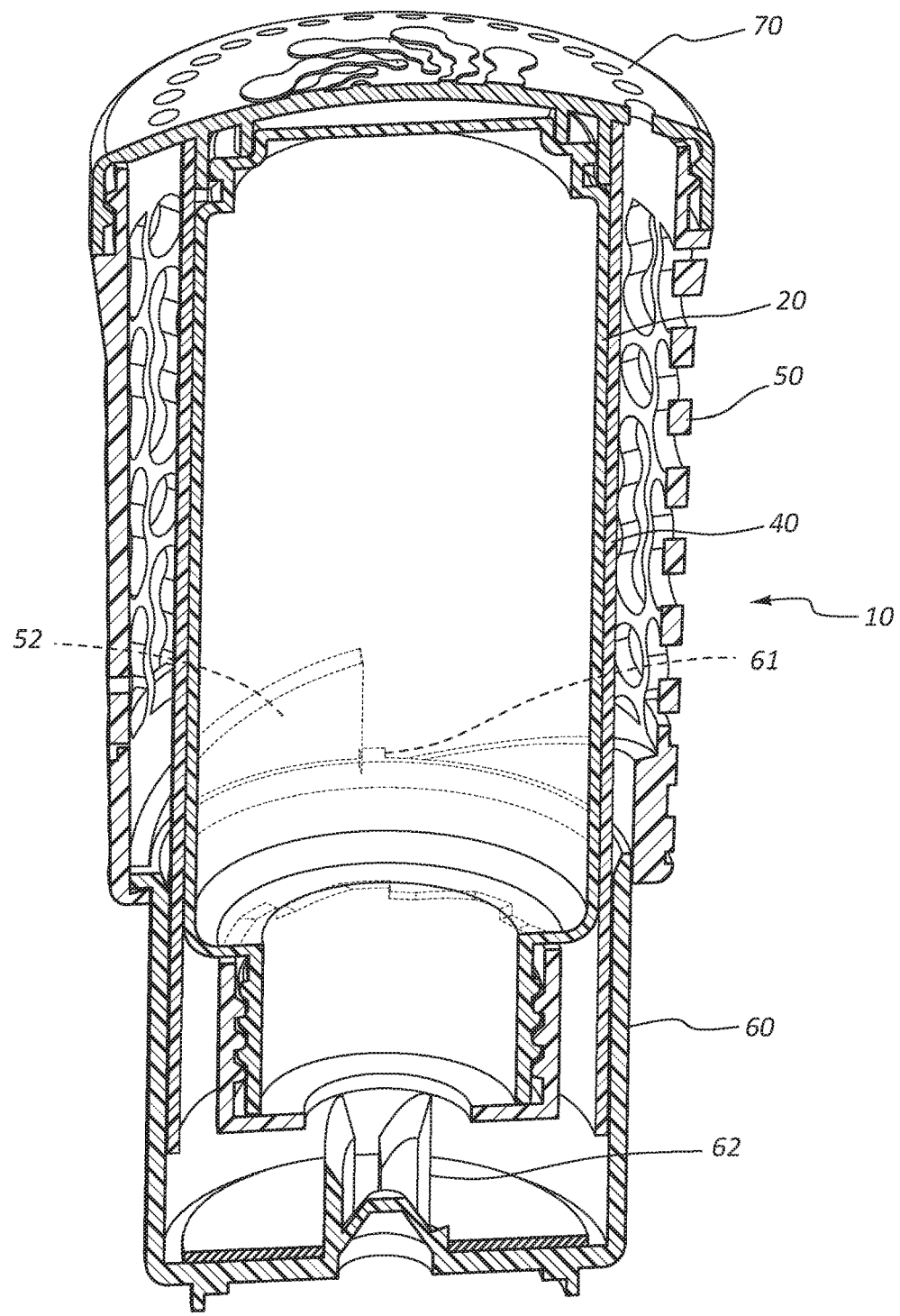
FIG. 15 is a cut-away isometric view of the twist activated dispenser.
Figure 16:
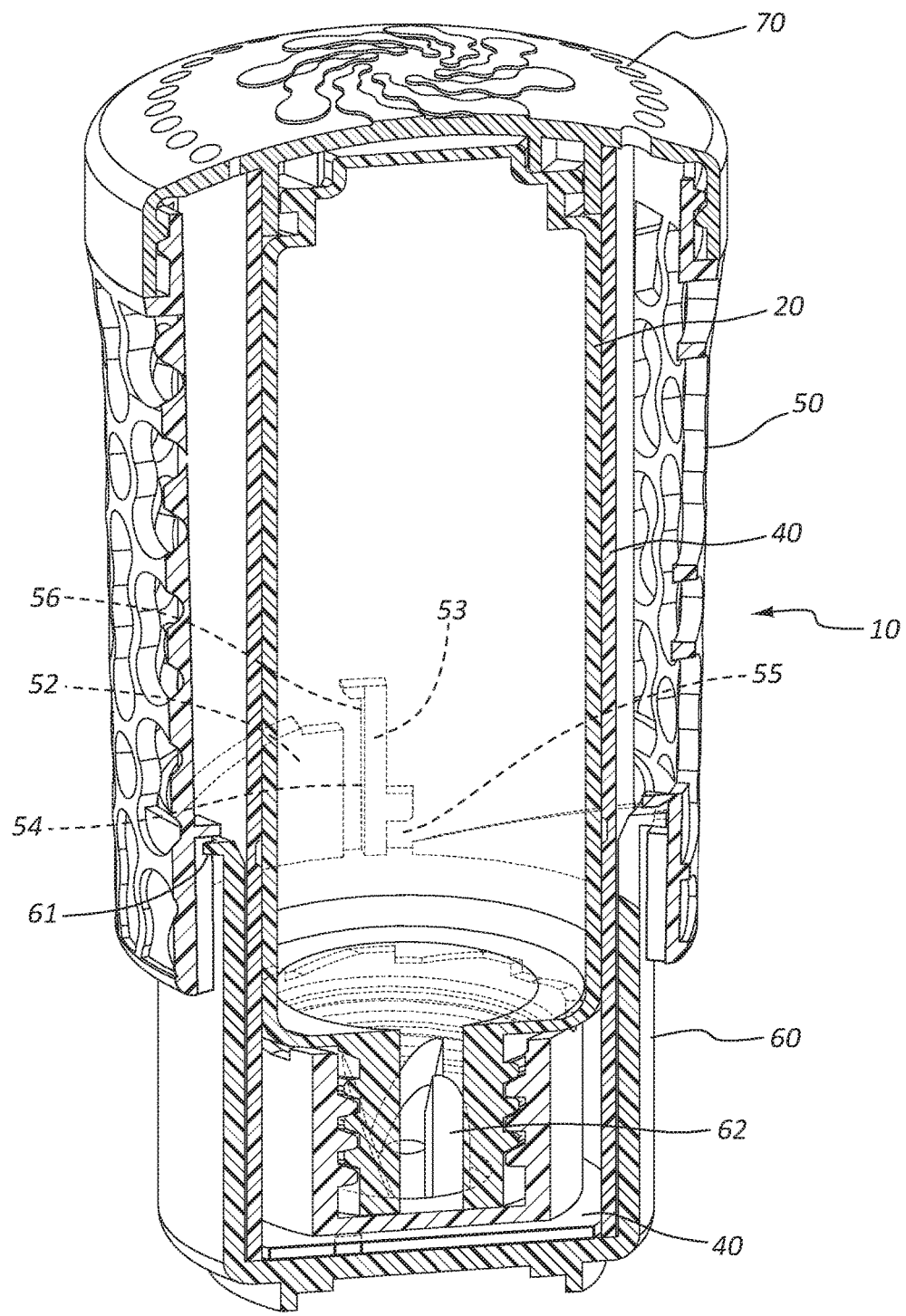
FIG. 16 is a cut-away isometric view of the twist activated dispenser in the activated position.
Figure 17:
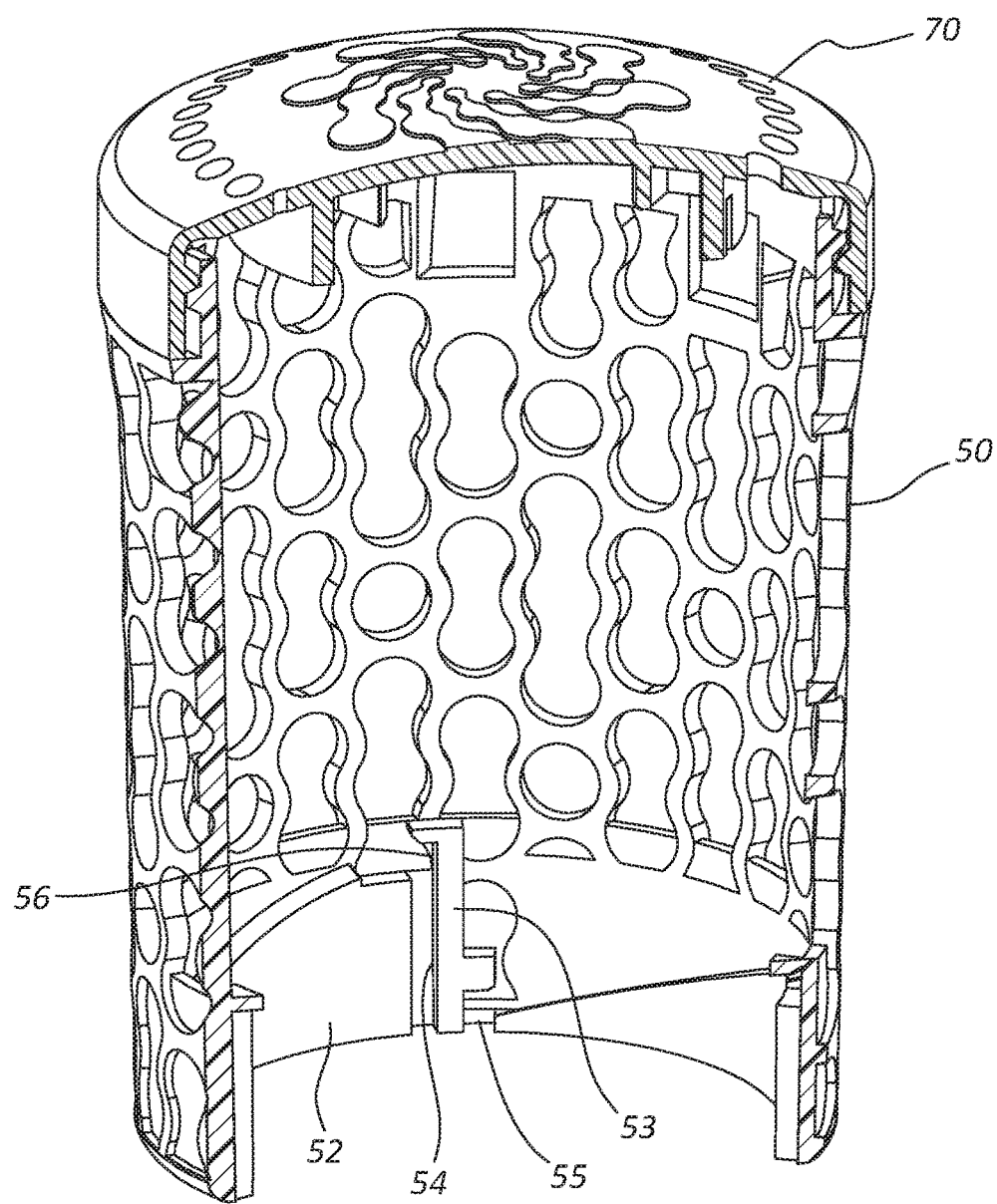
FIG. 17 is a cut-away isometric view of a cage for the twist activated dispenser.

FIGS. 15-17 illustrate the ramp mechanism in more detail. In the storage or inactive position, as shown in FIG. 15, the tabs 61 are positioned at the bottom or beginning of the set of ramps 52. The set of blades 62 remain below the seal 34 of the container 20. When the base 60 is rotated clockwise, the base 60 travels upward into the cage structure 50, or the cage structure 50 and base 60 are drawn together, collapsing the dispenser 10 on itself and pulling the set of blades 62 into the container 20 breaking the seal 34. The set of tabs 61 travel from the storage lock 55 along the set of ramps 52, pulling the base 60 into the cage structure 50 as the set of tabs 61 ride along the set of ramps 52 until they hit the blocking wall 54 of the stop 53, where the tab 61 falls into or rests in the locking groove 56. This position is referred to as the activated position, as shown in FIG. 16, where the set of blades 62 fully puncture the seal 34 of the container 20.

The internal components of the cage structure 50 with the lid 70 are shown in more detail in FIG. 17. The cage structure 50 includes the set of ramps 52 with a stop 53 positioned at the end of the ramp 52. The stop 53 has a backing wall 54 to stop the progress of the set of tabs 61 along the ramp, a storage lock 55 to hold the set of tabs 61 in the storage position until ready for use, and a locking groove 56 to hold the set of tabs 61 in the active position while in use.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A dispenser comprising:
 a container for storing a fluid, the container including a cap with a breakable seal, the cap attached to the container at a first end;
 a lid fixedly attached to a second end of the container, the lid having a set of vents;
 an absorbing device disposed around the outside of the container and cap;
 a cage structure attached to the lid and a base, the cage structure, lid and base collectively being configured to enclose the container, cap and absorbing device;
 the base including a set of blades positioned inside the base and aligned with the breakable seal in the cap; and
 the cage structure and base being connected with a rotational connection, when rotated with respect to each other, the cage structure and base are drawn together, collapsing the dispenser on itself and pulling the set of blades into the container and puncturing the breakable seal.

2. The dispenser of claim 1, wherein the cage structure and lid are connected with a fastening mechanism to prevent the cap from backing off.

3. The dispenser of claim 2, wherein the fastening mechanism includes a set of threads on the container and in the cap, and a set of teeth on the cap that engage a barb mechanism when tightened.

4. The dispenser of claim 1, wherein the cage structure includes threads and a set of teeth, and the lid includes matching threads and barbs, wherein the teeth on the cage structure engage the barbs when the lid is tightened against the cage structure.

5. The dispenser of claim 4, wherein the lid and container are attached with a locking fastener to fixedly attach the lid to the container, the lid being attached to the cage structure to position the cage structure around and spaced from the container.

6. The dispenser of claim 1, wherein the container includes a rib formed around the outer wall, the rib being configured to form a tight fit between the container and the absorbing device.

7. The dispenser of claim 6, wherein the cage structure includes a mesh configured to allow air to flow into the cage structure, the rib being positioned on the container aligned with the bottom edge of the mesh in the cage structure.

8. The dispenser of claim 1, wherein the cage structure includes a set of ramps and the base includes a set of tabs, the tabs slide along each ramp when the base is rotated with respect to the cage structure to draw the base and cage structure together.

9. The dispenser of claim 8, wherein the cage structure includes a stop at the end of each ramp, the stop being configured to prohibit further rotation and movement of each tab.

10. The dispenser of claim 9, wherein the stop includes a blocking wall disposed at the ramp, a storage lock to prevent movement of each tab when the dispenser is in an inactive position, and a locking groove to prevent movement of each tab when the dispenser is in an active position.

11. A dispenser comprising:
a container for storing a fluid, the container including a seal at a discharge end, the seal being made from a material capable of being penetrated;
a lid fixedly attached to a closed end of the container, the lid having a set of vents, the vents being arranged on the lid beyond an outer wall of the container;
an absorbing device disposed around the outer wall of the container;
a cage structure including the lid and a base, the cage structure being attached to the lid and base and combined to enclose the container and absorbing device;
the base including a set of blades positioned inside the base and aligned with the seal in the container;
the cage structure including a set of ramps and the base including a set of tabs, the base being placed in the cage structure with the tabs configured to slide along each ramp when the base is rotated with respect to the cage structure to draw the base and cage structure together; and
as the base is rotated, the set of blades travel into the container and puncture the seal.

12. The dispenser of claim 11, wherein the cage structure includes a stop disposed at the top of each ramp, the stop being configured to prevent movement of each tab beyond an end of the ramp.

13. The dispenser of claim 12, wherein the stop includes a blocking wall arranged to prevent movement of each tab beyond the ramp, a storage lock to prevent movement of each tab when the dispenser is in an inactive position, and a locking groove to prevent movement of each tab when the dispenser is in an active position.

14. The dispenser of claim 11, wherein the container includes a rib encircling the container, the absorbing device and rib being configured to create a snug fit around the container.

15. The dispenser of claim 14, wherein the cage structure includes a mesh configured to allow air to flow into the cage structure around the absorbing device, the rib being disposed on the container in a position to align the rib with the bottom edge of the mesh in the cage structure.

16. A dispenser comprising:
a container for storing a fluid, the container including a seal at a discharge end, the seal being made from a material capable of being penetrated;
an absorbing device including a wick disposed around an outer wall of the container;
a cage structure including a mesh portion, a lid and a base, the lid being fixedly attached to a closed end of the container and a first end of the mesh portion, the base being rotationally attached to a second end of the mesh portion, the cage structure being configured to enclose the container and absorbing device, the mesh portion being configured to allow air to flow into the cage structure around the wick, the base including a set of blades positioned inside the base and aligned with the seal in the container; and
the container including a rib formed around the container, the rib being configured to create a snug fit between the container and the wick.

17. The dispenser of claim 16, wherein the rib is formed on the container in a position to align the rib with a bottom edge of the mesh portion in the cage structure.

18. The dispenser of claim 16, wherein the cage structure includes a set of ramps and the base includes a set of tabs, the tabs are configured connect to the cage structure and to slide along each ramp when the base is rotated with respect to the cage structure to draw the base and cage structure together.

19. The dispenser of claim 18, wherein the cage structure includes a stop formed in the cage structure at the end of each ramp, the stop being configured to prevent movement of each tab beyond the stop.

20. The dispenser of claim 19, wherein the stop includes a blocking wall disposed at each ramp, a storage lock arranged to prevent movement of each tab when the dispenser is in an inactive position, and a locking groove arranged to prevent movement of each tab when the dispenser is in an active position.

* * * * *